United States Patent [19]
Kanner et al.

[11] Patent Number: 4,496,754
[45] Date of Patent: Jan. 29, 1985

[54] SILYL CARBAMATES AND SYNTHESIS THEREOF

[75] Inventors: Bernard Kanner, West Nyack; Steven P. Hopper, Mahopac, both of N.Y.; Dennis J. Sepelak, McMurray, Pa.

[73] Assignee: Union Carbide Corporation, Danbury, Conn.

[21] Appl. No.: 454,178

[22] Filed: Dec. 28, 1982

[51] Int. Cl.$^3$ .............................. C07F 7/10; C07F 7/18
[52] U.S. Cl. ..................................................... 556/420
[58] Field of Search ......................................... 556/420

[56] References Cited

U.S. PATENT DOCUMENTS 4,400,526  8/1983  Kanner et al. ...................... 556/420

FOREIGN PATENT DOCUMENTS 0486021  7/1976  U.S.S.R. .............................. 556/420
745904  7/1980  U.S.S.R. .............................. 556/420

OTHER PUBLICATIONS

Lappert and Prokai, Adv. Organometal. Chem., 5 (1967) 225.
Cragg and Lappert, J. Chem. Soc., A (1966) 82.
Berkofer and Sommer, J. Organometal Chem. 35, (1972) C 15.
Berkofer and Sommer, J. Organometal. Chem., 99, (1975) C1.
Sheludyakov et al., Zh. Obshch Khim., 47, (1977) 1515.
Jung and Lyster, J. Chem. Soc., Chem. Comm. (1978) 315.
Sheludyak et al., Zh. Obshch, Khim., 45, (1975) 479.

Primary Examiner—Paul F. Shaver
Attorney, Agent, or Firm—Paul W. Leuzzi, II

[57] ABSTRACT

Silyl carbamates are produced by the reaction under suitable reaction conditions of silanes bearing at least one silicon-hydrogen bond of the formula: $R_{4-x}SiH_x$ with an ammonium carbamate of the formula: $R'R''NH_2 \oplus R'R''NCO_2 \ominus$. This novel route is much simpler and more direct than those previously known and provides a new classes of silyl carbamates.

26 Claims, No Drawings

SILYL CARBAMATES AND SYNTHESIS THEREOF

BACKGROUND OF THE INVENTION

The instant invention is directed to a novel process for preparing silyl carbamates and novel silyl carbamates produced therefrom. More particularly, the instant invention is directed to a reaction between silyl hydrides and carbamates.

The preparation of silyl carbamates is generally accomplished by the insertion of carbon dioxide into the silicon-nitrogen bond of a silylamine. Although this insertion reaction was extensively studied in the sixties (Lappert and Prokai, Adv. Organometal, Chem., 5 (1967) 225,) the route has had limited attention and application because silylamines are frequently inconvenient and cumbersome to prepare. Other methods of limited appeal have been described in Cragg and Lappert, J. Chem. Soc. (A), (1966) 82; Berkofer and Sommer, J. Organometal Chem., 35 (1972) C15; and the literature set forth below. Accordingly, there exists the need for a more direct and facile method for preparing silyl carbamates.

Silyl carbamates themselves are well known in the art as reactive intermediates to a variety of useful products. In 1975 the reaction N,O-bis-(trimethylsilyl)carbamate with alcohols, phenols and carboxylic acids was reported to lead to the formation of trimethylalkoxy (and acetoxy) silanes, (L. Berkofer and P. Sommer, J. Organometal Chem., 99 (1975) C1). Mironov's group studied o-silylurethanes in some detail during the seventies. These workers noted that "all O-silylurethanes are readily hydrolyzed air, with the exception of $PhNHCO_2SiMe_3$ which is surprisingly stable in air" (V. O. Sheludyakov, A. D. Kirilin, A. I. Gusev, V. A. Sharapov and V. F. Mironov, Zh, Obshch. Khim., 46 (1976) 2712). Methanol reacts with O-(trimethylsilyl) carbamates leading to the formation of trimethylmethoxysilane, carbon dioxide and an amine (M. E. Jung and M. A. Lyster, J. Chem. Soc., Chem. Comm. (1978) 315 and references therein). While the literature thus far cited is related to a few of the products which this invention can prepare, none of the work cited in the literature used the interaction of a silyl hydrogen and a carbamate to affect the synthesis of the silyl carbamate. Furthermore, there is no teaching of the preparation of alkoxysilylcarbamates and dicarbamates.

SUMMARY OF THE INVENTION

The present invention provides a process for preparing silyl carbamates which comprises reacting under suitable reaction conditions one or more silanes selected from the group of silanes represented by the general formula:

$$R_{4-x}SiH_x$$

wherein R is individually an aliphatic or aromatic, saturated or unsaturated hydrocarbon or alkoxy radical containing from one to twelve carbon atoms, inclusive, and x has a value of from one to two; with one or more ammonium carbamates or corresponding carbamic acid compounds selected from the group of ammonium carbamates represented by the general formula:

$$R'R''NH_2^{\oplus} R'R''NCO_2^{\ominus}$$

or from the group of carbamic acids represented by the general formula:

$$R'R''NCOOH$$

wherein R' and R'' are individually hydrogen or an aliphatic saturated or unsaturated hydrocarbon radical containing from one to twelve carbon atoms inclusive and thereafter recovering said silyl carbamate, said silyl carbamate being represented by the general formula:

$$R_{4-x}Si(O_2CNR'R'')_x$$

wherein R, R', R'', and x are as previously defined. This novel process provides a simple route to prepare silyl carbamates, certain classes of which are previously unknown. The novel classes of silyl carbamates which are now accessible via the process set forth above are represented by the formula $$R_{4-x}Si(O_2CNR'R'')_x$$

wherein R, R', R'' and x are as previously defined and where at least two R groups are alkoxy groups.

DETAILED DESCRIPTION OF THE INVENTION

In accordance with the present invention there is provided a novel process for the synthesis of silyl carbamates. The process comprises reacting silanes with ammonium carbamates or the corresponding carbamic acid compound wherein the silanes are of the general formula:

$$R_{4-x}SiH_x$$

wherein R is individually an aliphatic or aromatic, saturated or unsaturated hydrocarbon or alkoxy radical containing from one to twelve carbon atoms, inclusive. Preferably, R is individually an aliphatic, saturated, unsubstituted radical or alkoxy radical having from one to eight carbon atoms, inclusive. The value of x can range from one to two.

Suitable silanes expected to be useful in the present invention include, but are not limited to, dimethylsilane, trimethylsilane, diethylsilane, triethylsilane, diphenylsilane, triphenylsilane, methylethylsilane methylethylphenylsilane, methyldiphenylsilane, 1-methyl-1-silacyclobutane, 1-silacyclopentane, dimethoxysilane, trimethoxysilane, diethoxysilane, triethoxysilane, di-i-propoxysilane, tri-i-propoxysilane, methoxyethoxysilane dimethoxy-t-butoxysilane, diethoxy-n-propoxysilane methyldimethoxysilane, dimethylethoxysilane phenylmethoxysilane, methyldimethoxysilane, ethyldiethoxysilane, ethyldimethoxysilane, phenyldiethoxysilane, phenyldimethoxysilane, methyldi-i-propoxysilane, didodecylsilane, methyldioctylsilane, trinonylsilane, dodecyldimethoxysilane, tri-p-tolylsilane, allyldimethylsilane, allyldiethoxysilane and the like.

These silanes are commercially available or they may be prepared in accordance with known techniques such as set forth by Bazant et al. in "Organosilicon Compounds", 1965 or Eaborn, "Organosilicon Compounds", 1960.

The ammonium carbamates that react with the silanes are of the general formula:

$$R'R''NH_2^{\oplus} R'R''NCO_2^{\ominus}$$

wherein R' and R" are individually of the same significance as previously set forth. It is preferred that R' and R" individually be hydrogen or alkyl group containing from one to six carbon atoms inclusive.

Suitable ammonium carbamates expected to be useful in the present invention include, but are not limited to, ammonium carbamate, methylammonium methylcarbamate dimethylammonium dimethylcarbamate, ethylammonium ethylcarbamate, diethylammonium diethylcarbamate, methylethylammonium methylethylcarbamate, propylammonium propylcarbamate, dipropylammonium dipropylcarbamate, allylammonium allylcarbamate, diallylammonium diallylcarbamate, cyclohexylammonium cyclohexylcarbamate, 2-methoxyethylammonium-2-methoxyethyl carbamate, bis-2-methoxyethylammonium-bis-2-methoxyethyl carbamate and the like.

These ammonium carbamates may be prepared in accordance with known techniques. Such compounds can be prepared by the reaction of amines with carbon dioxide which yields the ammonium carbamate or its corresponding carbamic acid compound of the formula:

R'R"NCOOH

Such techniques have been described in U.S. Pat. Nos. 2,915,569; 2,927,128; and 2,927,129.

The reaction temperature normally is kept between 0° C. and 60° C. although the process can be run within the broad temperature range of about −50° C. to 150° C. and, under special circumstances, perhaps higher. No special advantages are seen in operating at higher temperatures. The temperature should, however, preferably not reach the decomposition temperature of the ammonium carbamate being utilized.

A solvent may be desirable in some circumstances, although it is not usually required in the practice of the invention. Useful solvents would include a common hydrocarbon or etherial solvents, such as hexane or tetrahydrofuran, or a halocarbon solvent such as trichloroethylene.

Although atmospheric pressure is preferred, subatmospheric and superatmospheric pressures can be employed. It should be noted that pressure is not believed to be a critical parameter. The duration of the reaction may also vary with faster reactions occuring at higher temperatures and slower reactions at the lower temperatures. The time may vary from ten minutes or slower to over 24 hours although reactions within this time span are the favored practice.

The resulting silyl carbamate has the general formula:

R$_{4-x}$Si(O$_2$CNR'R")$_x$ wherein R, R', R" and x are as defined above. Process by-products include evolved hydrogen gas and amines of the generic formula:

R'R"NH wherein R' and R" and as set forth above. The silyl carbamate can be isolated from the by-products from any of a variety of known techniques, as illustrated in the examples. Exemplary silyl carbamates prepared by the present process include, but are not limited to, dimethyldimethylcarbamatosilane, trimethyldiethylcarbamatosilane, diethyldimethylcarbamatosilane, triethylmethylcarbamatosilane, dipropyldicarbamatosilane, tributylcarbamatosilane, methylethylmethylpropylcarbamatosilane, methylethylpentyldimethyl carbamatosilane, methyldibutylcarbamatosilane, 1-methyl-1-dimethyl-carbamato-1-silacyclobutane, 1-methylcarbamato-1-silacyclopintane, dimethoxyldimethylcarbamatosilane, trimethoxydiethylcarbamatosilane, diethoxydimethylcarbamatosilane, triethoxydimethylcarbamatosilane, di-i-propoxymethyl carbamatosilane, tri-i-propoxycarbamatosilane, methoxyethoxydimethylcarbamatosilane, dimethoxy-t-butoxymethylcarbamatosilane, methyldimethoxydimethylcarbamatosilane, methylethoxydiethylcarbamatosilane, hexyldimethoxycarbamatosilane and the like.

Silyl carbamates such as are prepared in accordance with the instant invention find utility as reactive intermediates to a variety of commercial products. Birkofer and Sommer, J. Organometal. Chem. 99 (1975) C1, sets forth some of these reactions.

The instant invention also provides a novel class of silyl carbamates of the general formula:

R$_{4-x}$Si(O$_2$CNR'R")$_x$ wherein R is individually selected from the group consisting of methoxy, ethoxy, i-propoxy, methyl, ethyl or phenyl groups; R' and R" are individually selected from the group consisting of methyl, ethyl, propyl and butyl groups; and x is one or two.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

EXAMPLES ONE AND TWO

Preparations and Isolation of
N,N-dimethylcarbamatotriethoxysilane

Two reactions were carried out in an identical fashion except one was stirred at room temperature and required 24 hours to fully consume the triethoxysilane. The second reaction was stirred at 50° C. and required three hours to fully consume the triethoxysilane. The latter reaction was described in detail in example.

A round bottomed, three necked, 50 ml flask equipped with a magnetic stirring unit, thermometer and constant pressure addition funnel was flushed with argon. The flask was then charged with 7.8 gm (48 mmole) of triethoxysilane and 6.3 gm (48 mmole) of dimethylammonium dimethylcarbamate. The flask an its contents were heated with stirring under argon by means of a heating mantle to 50° C. As determined by glpc the triethoxysilane was consumed after three hours at 50° C. As determined by normalized area percent and retention times, the reaction produced 22% tetraethoxysilane, and 78% N,N-dimethylcarbamatotriethoxysilane. The reaction at room temperature produced the same two products in 31% and 69% yields respectively.

The two reaction mixtures were combined for vacuum fractional distillation. A fraction of tetraethoxysilane, 3.2 gm (16% based on total starting triethoxysilane) was collected with bp 34°/5 mm. A fraction of N,N-dimethylcarbamatotriethoxysilane, 9.3 gm (38%) was collected with bp 72°-94°/5 mm. The latter product was identified by nmr and glpc which indicated a trace, less than 5%, of the other materials.

EXAMPLE THREE

Preparation of N, N-dimethylcarbamatotriethoxysilane in the Presence of Tetraethoxysilane and Analysis by Conversion to Tetraethoxysilane This example utilized the initial presence of tetraethoxysilane to minimize its formation during the course of the reaction between triethoxysilane and dimethylammonium dimethylcarbamate. The reaction was carried out as in Example One at 50°. Before reaction, an internal standard yield analysis indicated the presence of 4.3 gm of tetraethoxysilane. After 3.5 hrs at 50° C. the internal standard yield analysis gave an identical result. Excess ethanol was added to the reaction mixture to convert the carbamate product to tetraethoxysilane. A final internal yield analysis indicated the presence of 9.5 gm of tetraethoxysilane. This result implies the formation of N,N-dimethylcarbamatotriethoxysilane in a minimum of 73% based on triethoxysilane charged.

EXAMPLE FOUR

Reaction between Triethysilane and Dimethylammonium Dimethylcarbamate

A 50 ml, round bottomed, three necked flask equipped with a magnetic stirring unit, a septum and a reflux condenser topped with an argon inlet was charged with 10.3 gm (189 mmole) of triethylsilane and 10.0 gm (77 mmole) of dimethylammonium dimethylcarbamate. The flask and its contents were heated by means of an external oil bath with stirring under argon for a total of 18 hours at 53° and 24 hours at 59°. Examination of the reaction mixture by glpc indicated the slow loss of triethylsilane and formation of essentially one product. After the first heating period, additional dimethylammonium dimethylcarbamate was added. No triethylsilane remained, as evidence by glpc, after the second heating period. Vacuum fractional distillation yield 1.7 gm of material, bp 82°-89° C./1 mm which was pure and had the retention time which corresponded to the single product. Subsequent distillation appears to lead to decarboxylation of the product as evidence by the collection of fractions bp 95°-97°/mm (8.3 gm) and 87°-90°/3 mm (4.7 gm) whose retention times where 2 minutes shorter than the original single product.

EXAMPLE FIVE

Reaction Diethylsilane and Dimethylammonium Dimethylcarbamate

A 25 ml, round bottomed, three necked flask equipped with a magnetic stirring unit and a reflux condenser topped with a nitrogen inlet was flushed with nitrogen. Diethylsilane, 3.8 gm (43.1 mmole) and dimethylammonium dimethylcarbamate, 11.4 gm (86.2 mmole) were charged into the flask and stirring under nitrogen was commenced. The initially incompatible mixture became compatable and a rapid gas evolution was noted. The reaction mixture exothermed from 22° C. to a maximum of 29°. After stirring for one hour after mixing, the reaction mixture was homogeneous and analysis by glpc indicated the absence of starting silane. The reaction mixture was heated at 50° C. overnight to ensure complete conversion. After stripping at aspirator vacuum there remained 6.4 gm (57%) of water white liquid whose nmr was consistent with that expected for bis-(N,N-dimethylcarbamato)diethylsilane. The infrared spectra of the product contained a CO at 1680 cm$^{-1}$.

EXAMPLE SIX

Preparation of Diethyldimethoxysilane via the Intermediate bis(N,N-dimethylcarbamato) diethylsilane The title bis-(N,N-dimethylcarbamato)-diethylsilane was prepared in 57% isolated yield from the reaction of 3.8 gms (43.1 mmoles) of diethylsilane and 11.4 gm (86.2 mmole) of dimethylammonium dimethylcarbamate. A rapid gas evolving reaction occurred upon mixing the reagents and the reaction mixture was heated to insure complete reaction. Low boiling residues were removed by rotary evaporation.

The nmr spectrum of the crude material was in accord with its structure. The product's identity was further confirmed by its chemical transformation to diethyldimethoxysilane as follows: methanol, 1.2 gm (37.5 mmole) was mixed with the crude product above, 4.9 gm (18.7 mmole). After 20 minutes stirring the reaction mixture was simple distilled to give a fraction, 2.7 gm, containing 2.2 gm (88%) of dimethylammonium dimethylcarbamate, b.p. 60° and 0.5 gm (18%) of diethyldimethoxysilane. The pot residue, 2.3 gm (83%), was the latter silane in high purity. The nmr spectra of the pot residue was in good accord with the structure proposed.

EXAMPLE SEVEN

Preparation of Diethyldimethoxysilane via the Intermediate bis-(N,N-diethylcarbamato)diethylsilane Diethylsilane, 2.6 gm (29.5 mmole), and diethylammonium diethylcarbamate, 11.2 gm (59.0 mmole) were reacted as described in Example Six. The solid carbamate was heated with a heat gun and added to the silane as the melt. Gas evolution was evident upon mixing. The reaction mixture was heated with stirring under nitrogen overnight. Simple distillation yielded 5.6 gm (77 mmole) of diethylamine, b.p. 60° C. and identified by its glpc retention time and b.p. The pot residue 4.5 gm (58%) was determined to be the title carbamate by nmr and subsequent chemical transformation to the title silane. Diethyldimethoxysilane was prepared by reaction of 3.3 gms of the above pot residue with a 20 mole percent excess of methanol. In addition to a resonance at 3.32 the nmr of the resulting mixture contained only resonances characteristic of diethyldimethoxysilane and diethylammonium diethylcarbamate. The spectral characterization utilized comparison to the spectra of authentic, independently prepared samples of both materials.

EXAMPLE EIGHT

Preparation of Tetraethoxysilane via the Intermediate N,N-diethylcarbamatotriethoxysilane A 50 ml, round bottomed, three necked flask equipped with a magnetic stirring inlet, thermometer, constant pressure addition funnel and a reflux condenser topped with a nitrogen inlet was flushed with nitrogen. The flask was then charged with 9.0 gm of a mixture of triethoxysilane (44.4 mmole) and tetraethoxysilane (8.2 mmole). The addition funnel was charged with 8.4 gm (44.4 mmole) of solid diethylammonium diethylcarbamate. The carbamate was melted by means of a heat gun and added to the reaction vessel as the melt. The reaction vessel was equipped with a simple distillation apparatus and heated to 80° C. Diethylamine, 1.9 gm (59% of the total diethylamine groups charged) was collected at 60° C. and identified by its glpc retention time and bp. The reaction vessel was the evacuated and 2.7 gm of tetraethoxysilane was collected with bp 27°/0.22 mm and shown by glpc retention time and area percent to be very pure tetraethoxysilane. Since the reaction mixture initially contained 8.2 mmole of tetraethoxysilane, the isolated yield of 13.0 mmole of the latter silane indicates that the reaction produced 4.8 mmole (11%) of tetraethoxysilane. The nmr of the crude pot residue was in accord with the title carbamate. A sample of the pot residue, 6.0 gm (21.5 mmole) was treated with 1.01 gm (21.5 mmole) of ethanol. Internal standard yield analysis using octane as a standard indicated the formation of 18.2 mmoles (85%) of tetraethoxysilane. Internal standard yield analysis on diethylamine, the glpc thermal decomposition product of the diethylammonium diethylcarbamate formed in the displacement reaction with ethanol, indicated the presence of 19.6 mmole (91%) of the amine.

EXAMPLE NINE

Preparation of N,N-Diethylcarbamatotrimethoxysilane

A round bottomed, three neck 50 ml flask was fitted with a magnetic stirring unit, constant pressure addition funnel and a reflux condenser topped with an inert gas inlet. The flask was charged with a mixture of about 40 mmole of trimethoxysilane and 7 mmole of tetramethoxysilane. Diethylammonium diethylcarbamate, 8.8 gm (46.5 mmole) was added and the mixture was stirred at room temperature overnight. Examination of the reaction mixture of glpc revealed the complete consumption of trimethoxysilane and the formation of N,N-diethylcarbamatotrimethoxysilane in at least 50% yield.

EXAMPLE TEN

Reaction between Triethoxysilane and Diethylammonium Diethylcarbamate

The procedure of Example Nine was followed for the reaction between 3.5 gm (21.1 mmoles) of triethoxysilane and 4.0 gm (21.1 mmole) of diethylammonium diethylcarbamate. Upon the completion of the addition the reaction mixture was stirred for only four (4) hours at room temperature. At this time the reflux condenser was replaced by a microdistillation head and the reaction mixture was heated to 75°–80° C. for three (3) hours. During the time 1.3 gm (84%) of diethylamine was distilled from the reaction mixture. Upon cooling to room temperature the reaction mixture, 5.1 gm, was analyzed using the internal standard yield analysis method in an all glass 8 ft.×¼ inch column packed with 3% OV-1 operating isothermally at 150° C. Analysis indicated the presence of 4.5% unreacted triethoxysilane; 24.5% tetraethoxysilane; 56.3% N,N-diethylcarbamatotriethoxysilane; and 7.9% bis-(N,N-diethylcarbamato)diethoxysilane. All of the materials quantified in the analysis were identified after collection from the column by their retention times on an analytical column (10% SE-30) and their nmr spectra.

We claim:

1. A process for preparing silyl carbamates which comprises reacting, under suitable reaction conditions, one or more silanes represented by the general formula:

$$R_{4-x}SiH_x$$

wherein R is individually an aliphatic or aromatic, saturated or unsaturated hydrocarbon or alkoxy radical containing from one to twelve carbon atoms, inclusive, and x has a value of from one to two; with one or more ammonium carbamates or corresponding carbamic acid compounds selected from ammonium, carbamates represented by the general formula:

$$R'R''NH_2^{\oplus}R'R''NCO_2^{\ominus}$$

or from the group of carbamic acid compounds represented by the general formula:

$$R'R''NCOOH$$

wherein R' and R'' are individually hydrogen or an aliphatic saturated or unsaturated hydrocarbon radical containing from one to twelve carbon atoms inclusive, and thereafter recovering, said silyl carbamate, said recovered silyl carbamate being represented by the general formula:

$$R_{4-x}Si(O_2CNR'R'')_x$$

wherein R, R', R'' and x are as previously defined.

2. The process of claim 1 wherein the silane is one in which R is individually an aliphatic, saturated hydrocarbon or alkoxy radical wherein said radicals contain from one to eight carbon atoms.

3. The process of claim 1 wherein the ammonium carbamate is one in which R' and R'' are individually hydrogen or alkyl groups containing from one to six carbon atoms.

4. The process of claim 1 wherein the reaction occurs at a temperature within about −50° C. to about 150° C.

5. The process of claim 4 wherein the reaction temperature is within about 0° C. to about 60° C.

6. The process of claim 1 wherein there is employed a solvent.

7. A process for preparing silyl carbamates which comprises reacting one or more silanes represented by the general formula:

$$R_{4-x}SiH_x$$

wherein R is individually an aliphatic, saturated hydrocarbon or alkoxy radical wherein said radicals contain from one to eight carbon atoms and x has a value of from one to two; with one or more ammonium carbamates or its corresponding carbamic acid compound selected from ammonium carbamates represented by the general formula:

$$R'R''NH_2^{\oplus}R'R''NCO_2^{\ominus}$$

wherein R' and R'' are individually hydrogen or alkyl groups containing from one to six carbon atoms, said process taking place under suitable reaction conditions and at a temperature between about 50° C. to about 150° C. and thereafter recovering said silyl carbamate, said recovered silyl carbamate being represented by the general formula $$R_{4-x}Si(O_2CNR'R'')_x$$

8. The process of claim 7 wherein the temperature is within the range of from about 0° C. to about 60° C.

9. The process of claim 7 wherein there is employed a solvent.

10. The process of claim 7 wherein the silyl carbamate is recovered by distillation.

11. A novel silyl carbamate represented by the general formula:

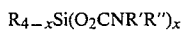

wherein R is individually selected from the group consisting of methoxy, ethoxy, and i-propoxy groups; R' and R" are individually selected from the group consisting of methyl, ethyl, propyl and butyl groups; and x is one or two.

12. The silyl carbamate of claim 10 wherein x is equal to one and wherein each R is individually an alkoxy group selected from the group consisting of methoxy, ethoxy, and i-propyl groups.

13. The silyl carbamate of claim 10 wherein x is equal to one and wherein one R is an alkyl group selected from the group consisting of methyl, ethyl and phenyl groups and wherein the remaining two R groups are individually alkoxy groups selected from the group consisting of methoxy, ethoxy and i-propoxy groups.

14. The silyl carbamate of claim 10 wherein x is equal to two and wherein each R is individually an alkoxy group selected from the group consisting of methoxy, ethoxy, and i-propoxy.

15. N,N-dimethylcarbamatotrimethoxysilane.
16. N,N-diethylcarbamatotriethoxysilane.
17. N,N-dimethylcarbamatotri-i-propoxysilane.
18. N,N-dimethylcarbamatodiethoxymethylsilane.
19. N,N-diethylcarbamatodimethoxymethylsilane.
20. bis-(N,N-dimethylcarbamato)-dimethoxysilane.
21. bis-(N,N-diethylcarbamato)-diethoxysilane.
22. N,N-diethylcarbamatotrimethoxysilane.
23. N,N-dimethylcarbamatotriethoxysilane.
24. bis-(N,N-diethylcarbamato)-dimethoxysilane.
25. bis-(N,N-dimethylcarbamato)-diethoxysilane.
26. N,N-diethylcarbamatotri-i-propoxysilane.

* * * * *

UNITED STATES PATENT AND TRADEMARK OFFICE
CERTIFICATE OF CORRECTION

PATENT NO. : 4,496,754
DATED : January 29, 1985
INVENTOR(S) : Kanner, et al

It is certified that error appears in the above-identified patent and that said Letters Patent is hereby corrected as shown below:

Col. 1, line 34, change "hydrolyzed air" to -- hydrolyzed in air --.

Col. 4, line 56, change "an" to -- and --.

Col. 5, line 46, change "evidence" to -- evidenced --.

Col. 5, line 62, change "compatable" to -- compatible --.

Col. 7, line 6, change "was the" to -- was then --.

Signed and Sealed this

Third Day of September 1985

[SEAL]

Attest:

DONALD J. QUIGG

Attesting Officer    Acting Commissioner of Patents and Trademarks - Designate